United States Patent [19]

Odagiri et al.

[11] Patent Number: 5,190,047
[45] Date of Patent: Mar. 2, 1993

[54] PHOTOELECTRIC PULSATION TYPE PULSIMETER

[75] Inventors: Hiroshi Odagiri; Hiroyuki Masaki; Yuichi Inoue, all of Tokyo, Japan

[73] Assignee: Seiko Instruments Inc., Japan

[21] Appl. No.: 557,303

[22] Filed: Jul. 23, 1990

[30] Foreign Application Priority Data

Jul. 25, 1989 [JP] Japan ................... 1-193499
Jul. 25, 1989 [JP] Japan ................... 1-193501

[51] Int. Cl.⁵ ............................................. A61B 5/02
[52] U.S. Cl. ................................... 128/687; 128/689; 307/234
[58] Field of Search ............... 128/680, 687, 688, 689, 128/690, 706; 328/111; 307/234

[56] References Cited

U.S. PATENT DOCUMENTS 3,593,162 7/1971 Patmore ..................... 328/111
4,305,401 12/1981 Reissmueller et al. ............. 128/690
4,775,840 10/1988 Hideharu et al. ................... 328/111

FOREIGN PATENT DOCUMENTS 0332705 9/1989 European Pat. Off.
2327430 12/1973 Fed. Rep. of Germany .
1-01633 2/1989 Japan .
1425199 2/1976 United Kingdom .
2039364 8/1980 United Kingdom ............. 128/689

OTHER PUBLICATIONS

"Pulse-width monitor flags poor timing", Electronics International, vol. 54, No. 14, Jul. 1981, pp. 125-127.

Primary Examiner—William E. Kamm
Assistant Examiner—Scott M. Getzow
Attorney, Agent, or Firm—Bruce L. Adams; Van C. Wilks

[57] ABSTRACT

A photoelectric pulsation type pulsimeter irradiates the ray of light to a capillary blood vessel of a finger tip or the like and detects the level of the reflected ray of light changing with the pulsation as the pulsation. The present invention improves stability of the pulse rate display by disposing pulse width evaluation means between a pulsation detection circuit for detecting the pulsation and pulsation calculation means for measuring the period of the pulsation signal and calculating the pulse rate per minute.

The pulse width evaluation means evaluate the pulse signal outputted from the pulsation detection circuit and the pulse rate calculated by the pulsation calculation means.

12 Claims, 8 Drawing Sheets

FIG. 1
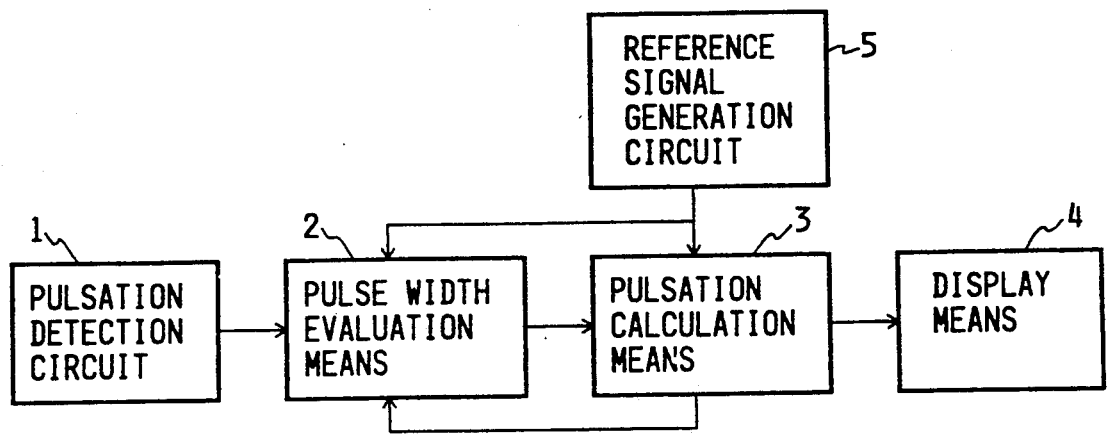
FIG. 2(A) PRIOR ART
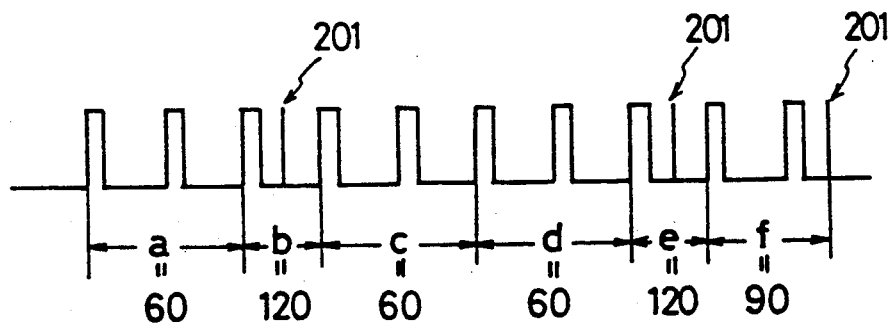
FIG. 2(B) PRIOR ART
| NO | DATA | Dmax | Dmin | D$_R$ | D$_N$ |
|---|---|---|---|---|---|
| 1 | a,b,c,d | a,b | c | d | 60 |
| 2 | b,c,d,e | b,e | c | d | 60 |
| 3 | c,d,e,f | e,f | c | d | 60 |

| NO | DATA | Dmax | Dmin | $D_R$ | $D_N$ |
|----|------|------|------|-------|-------|
| 1 | a,b,c,d | b,c | a | d | 90 |
| 2 | b,c,d,e | b,c | d | e | 120 |
| 3 | c,d,e,f | c,e | d | f | 120 |

PHOTOELECTRIC PULSATION TYPE PULSIMETER

BACKGROUND OF THE INVENTION

This invention relates to a photoelectric pulsation type pulsimeter.

Various attempts have been made in the past in order to stabilize the pulsation display of a portable pulsimeter. Most of them relate to a processing method of counted values when the pulse rate per minute is counted from the period of the pulsation signal obtained from a pulsation detection circuit. As an example, a processing system called a "4-data selection movement system" will be hereby explained. The 4-data selection movement system is a system which removes two values from the maximum value of the four pulsation conversion data $D_{max}$ and one value from the minimum value $D_{min}$ and displays one remaining data $D_R$ or $D_N$. A definite example is shown in FIG. 2. FIG. 2(A) shows the operation in the case where noise 201 exists intermittently in the output of the pulsation detection circuit. Symbols a, b, c, d, e and f in FIG. 2 represent the values converted to the pulse rate per minute from the average of the periods of two continuous pulsation signals. It can be understood from FIG. 2(B) that the display value $D_N$ is stable for the intermittent noises 201.

As described above, the prior art technique is effective for the intermittent noises, but are not effective for the continuous noise. FIG. 3(A) shows the operation when the continuous noise 301 exists. The output waveform of the pulsation detection circuit shown in FIG. 3(A) is exactly the same as that of FIG. 2(A) described above, but no effect at all is exhibited for the continuous noise 301. In accordance with such a method which eliminates the noise by data processing, the noise is also recognized as the pulsation signal and calculation-processed, which limits the stability and accuracy of the pulse rate display.

On the other hand, a LED or the like has been used conventionally as a light emission device of a pulsimeter for detecting the change of blood flow rate by use of optical means for counting and displaying a pulse rate. However, if a LED is turned on continuously during measurement, the consumed current becomes extremely great. Therefore, an attempt has been made to reduce the consumed current by continuously turning on the LED in a minimum light emission time in which light emission of the LED can be perceived as the change of the blood flow rate. The operation of this prior art device will be explained briefly with reference to a schematic structural view of a photoelectric pulsimeter shown in FIG. 8.

LED 111 is used as the light emission device, which continuously emits the rays of light from a light emission signal c from a CPU 118 through switching transistor 113. The intensity of the light is regulated by a current limiting resistor 112. The emitted infrared light impinges against a finger 114 of a subject, and the blood flow rate is converted to the level of reflected rays of light and transmitted to the light reception device 115. A phototransistor is used as this light reception device. Since the output of the phototransistor 115 generates a current in accordance with the intensity of the reflected rays, a resistor 116 generates a blood flow voltage a in accordance with the blood flow rate of the finger. This blood flow voltage a is amplified and shaped by an amplification circuit 117 and outputs the HPUL signal b which is in synchronism with the pulsation. The HPUL signal b is inputted to CPU 118, which calculates the pulse rate per unit time and the like from the input period of the HPUL signal and writes the date into a memory, not shown, or displays it. Reference numeral 119 represents a battery for supplying a current to each of the circuits described above.

If the battery is used as the power source of the pulsimeter for the measurement by use of the means described above, the internal resistance of the battery becomes high when the battery capacity drops or when the ambient temperature is low. In such a case, the power source voltage drops due to a voltage drop caused by the current flowing through the light emission device when it is turned on, and a spike pulse which is in synchronism with the turn-on of the light emission device, occurs in a waveform shaping circuit as the final output stage of the amplification circuit and is likely to overlap with the HPUL signal.

FIG. 9 shows the state described above. Under the normal state, the HPUL signal b is only the pulse signal which is in synchronism with the pulsation as shown in b-1. But if the spike pulse occurs for the reason described above, it overlaps on the HPUL signal as shown in b-2 and if CPU recognizes this spike pulse as the HPUL signal, it cannot calculate the pulsation correctly.

SUMMARY OF THE INVENTION

To solve the problem described above, the present invention interposes pulsation pulse width evaluation means for evaluating the pulse width of the pulsation signal outputted from a pulsation detection circuit between the pulsation detection circuit and pulsation calculation means on the basis of the pulse resulting from the noise has a relatively small pulse width.

As described above, the present invention includes the pulsation pulse width evaluation means and evaluates the pulsation signal outputted from the pulsation detection circuit so that only the signal which is recognized as the normal pulsation signal is transmitted to the pulsation calculation means. In this manner, the continuously inputted noise can be eliminated and stability of pulsation display is drastically improved. In addition, the present invention masks the HPUL signal in a specific period after the turn-on of the light emission device so as to prevent erroneous recognition of the spike pulse resulting from turn-on. The CPU does not erroneously recognize the spike pulse as the HPUL signal by employing the signal described above, but can recognize the correct HPUL signal which is in synchronism with the pulsation and thus can calculate the correct pulse rate.

BRIEF DESCRIPTION OF THE DRAWINGS

FIG. 1 is a block diagram showing an embodiment of the present invention;

FIGS. 2a and 2b are diagrams showing the operation of a 4-data selection movement system;

DETAILED DESCRIPTION OF THE PREFERRED EMBODIMENT

Figures 3A, 3B:
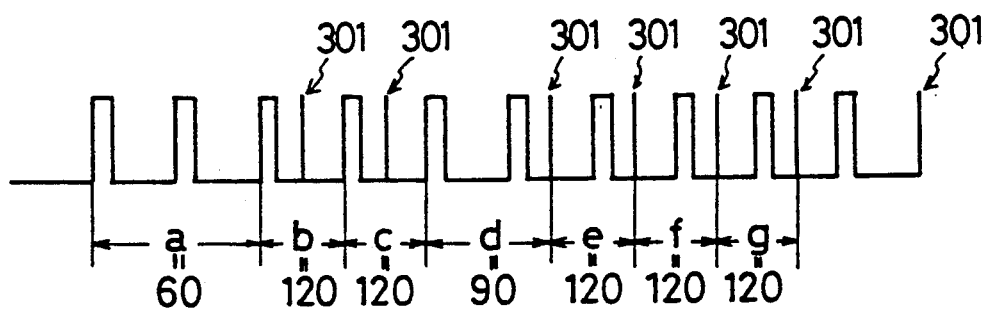
FIGS. 3a and 3b show the operation of the 4-data selection movement system when noises exist continuously.

FIG. 1 is a block diagram showing an embodiment of the present invention. A pulsation signal generated in response to a pulse detected by a pulsation detection circuit 1 is outputted to pulsation signal pulse width evaluation means 2. The pulsation signal pulse width evaluation means 2 evaluates the pulsation signal outputted from the pulsation detection circuit 1. An evaluation reference is determined from the pulse rate previously calculated by the pulsation calculation means 3 and displayed by the display means 4 and from a reference signal generation circuit 5. If the pulsation signal is found to have a pulse width above a reference pulse width as the result of the evaluation, the pulsation signal pulse width evaluation means 2 transmits a recognized pulsation signal to the pulsation counting means 3. The pulsation counting means calculates the pulse rate per minute from the period of the pulsation signal transmitted from the pulsation signal pulse width evaluation means 2 and outputs the result to the display means 4.

Figure 4A:
FIGS. 4a and 4b are diagrams showing the waveform of a pulsation detection circuit when a pulse rate is low.
Figure 4B:
Figure 5A:
FIGS. 5a and 5b are diagrams showing the waveform of the pulsation detection circuit when the pulse rate is high.
Figure 5B:

Since the pulsation signal pulse width evaluation means 2 is disposed as described above it generates a recognized pulsation signal, those signals which do not have a pulse width exceeding a certain pulse width are not recognized as the pulsation pulse, and the pulse rate display of the display means 4 becomes stabilized. Next, will be explained why a plurality of types of evaluation references are prepared for the pulsation signal pulse width evaluation means 2 depending on the content of the pulsation calculation means 3. If the pulsation detection circuit 1 consists of an amplification circuit, a filter and a simple waveform shaping circuit, when detecting photoelectric pulsation; the pulse width of the pulsation signal changes in accordance with the pulse rate as shown in FIG. 4 and 5. FIG. 4(A) and FIG. 5(A) show analog wave form and FIG. 4(B) and FIG. 5(B) show output wave form. The pulse width of the pulsation is small when the pulse rate is high and is great when the pulse rate is low. Therefore, if only one type of evaluation reference of the pulsation signal pulse width evaluation means 2 is used the evaluation reference must be set to a level which matches with the pulse width when the pulse rate is high. In which case, if the pulse rate is low, noise elimination performance drops.

Accordingly, the present invention employs the construction such that the evaluation reference of the pulsation signal pulse width evaluation means 2 changes with the level of the pulse rate.

Figure 6:
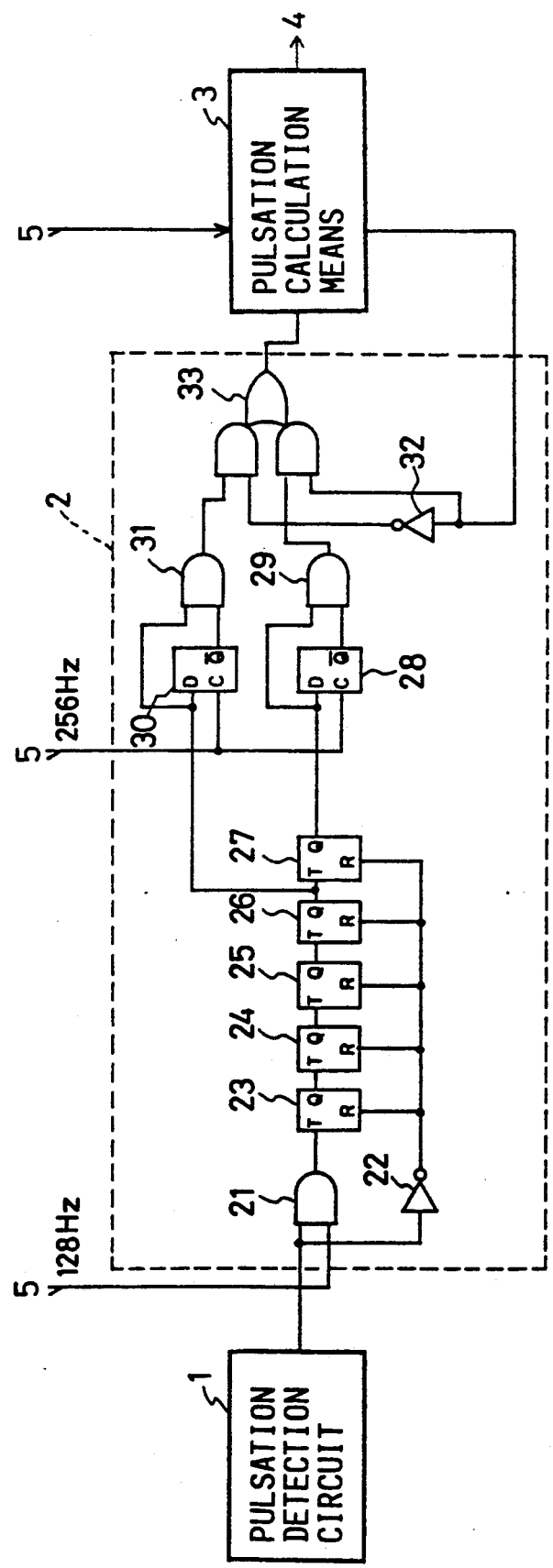
FIG. 6 show a first embodiment of the present invention.

FIG. 6 shows a detailed first embodiment of the pulsation signal pulse width evaluation means. Since the pulsation detection circuit 1 and the pulsation counting means are conventional, their detailed descriptions is omitted. While the pulsation signal pulse outputted from the pulsation detection circuit 1 is "1", a reference frequency from a reference signal generation circuit 5, such as 128 Hz, is outputted to the output of an AND gate 21. While the pulsation signal pulse is "1", the reset of a binary counter consisting of T-type flip-flops (hereinafter referred to as "TFF") 23-27 is released and TFF 23-27 count the 128 Hz output of the AND gate 21. When eight 128 Hz outputs of the AND gate 21 are counted, the Q output of TFF 26 rises to "1". Since the Q output of TFF 26 is connected to a differential circuit consisting of a D-type flip-flop (hereinafter referred to as "DFF") and an AND gate 31, a pulse signal having a certain width is generated at the output of the AND gate 31 the instant that the Q output of TFF 26 becomes "1". Since 256 Hz from the reference signal generation circuit 5 is connected to the clock terminal C of DFF 30, the pulse width of this pulse signal generates a signal having a pulse width of 1.95 ms. The time until the generation of the pulse at the output of this differential circuit is about 62.5 ms from the output of the pulsation signal to the output of the pulsation detection circuit 1. This time is uncertain because the output of the pulsation signal of the pulsation detection circuit 1 and the signal of the reference signal generation circuit 5 are not in synchronism with each other. Because they are asynchronous, the error of the pulse rate generated is about ±6 at the pulse rate of about 210. One of the methods of reducing this error is to use a higher frequency 128 Hz than the signal used inputted to the AND gate 21.

After the pulse is generated at the output of the AND gate 31 after the passage of about 62.5 ms, eight 128 Hz outputs of the AND gate 21 are further counted and then the Q output of the TFF 27 rises to "1". Since the Q output of the TFF 27 is connected to a differential circuit consisting of a DFF 28 and an AND gate 29, a signal having a pulse width of 1.95 ms is generated at the output of the AND gate 29 the instant the Q output of TFF 27 becomes "1". The time until the generation of the pulse at the output is about 125 ms after the output of the pulsation signal to the output of the pulsation detection circuit 1. The output of the AND gate 31 after the passage of about 62.5 ms and the output of the AND gate 29 after the passage of about 125 ms are connected to a multiplexer consisting of AND/OR gate 33 and an inverter 32. The multiplexer outputs the output of the AND gate 31 or 29 to the pulsation calculation means 4 in accordance with the control signal from the pulsation counting means 4. If the pulsation counting means 4 is constituted so that the control signal becomes "1" when the previous calculation result of the pulsation counting means is below the pulse rate of 100 and "0" when the latter is above the pulse rate of 100, the pulsation calculation means 4 makes the pulsation calculation when there is the input of the pulsation signal having a pulse width of at least about 125 ms when the pulse rate is below 100. It makes the pulsation calculation when there is the input of the pulsation signal having a pulse width of at least about 62.5 ms when the pulse rate is about 100.

If the pulsation pulse width evaluation means 2 is disposed between the pulsation detection circuit 1 and the pulsation calculation means 4 described above, the pulse rate can be counted by the pulsation signal having a pulse width above a certain predetermined width. As a result, the noise having a small pulse width is neglected, the pulsation display can be made stable. Two kinds of pulse width evaluation reference values for the pulsation signal are used in this embodiment, so that the pulsation signal can be easily increased and noise elimination performance can be improved further by so doing. When the pulse rate is high or when the pulse width of the pulsation signal is relatively small, measurement might be impossible if a long evaluation reference is applied. However, this can be easily solved by a method which selects the values of the evaluation reference values and the reference values, and thus alleviates measurement problems. For example, if the pulsation rate cannot be easily obtained; it is possible to employ a method which automatically selects a minimum evaluation reference value. In this type of pulsimeter, the pulse width evaluation means has storing means for storing a minimum evaluation reference value and selecting means for selecting a evaluation reference value from data stored in the storing means.

Figure 7:
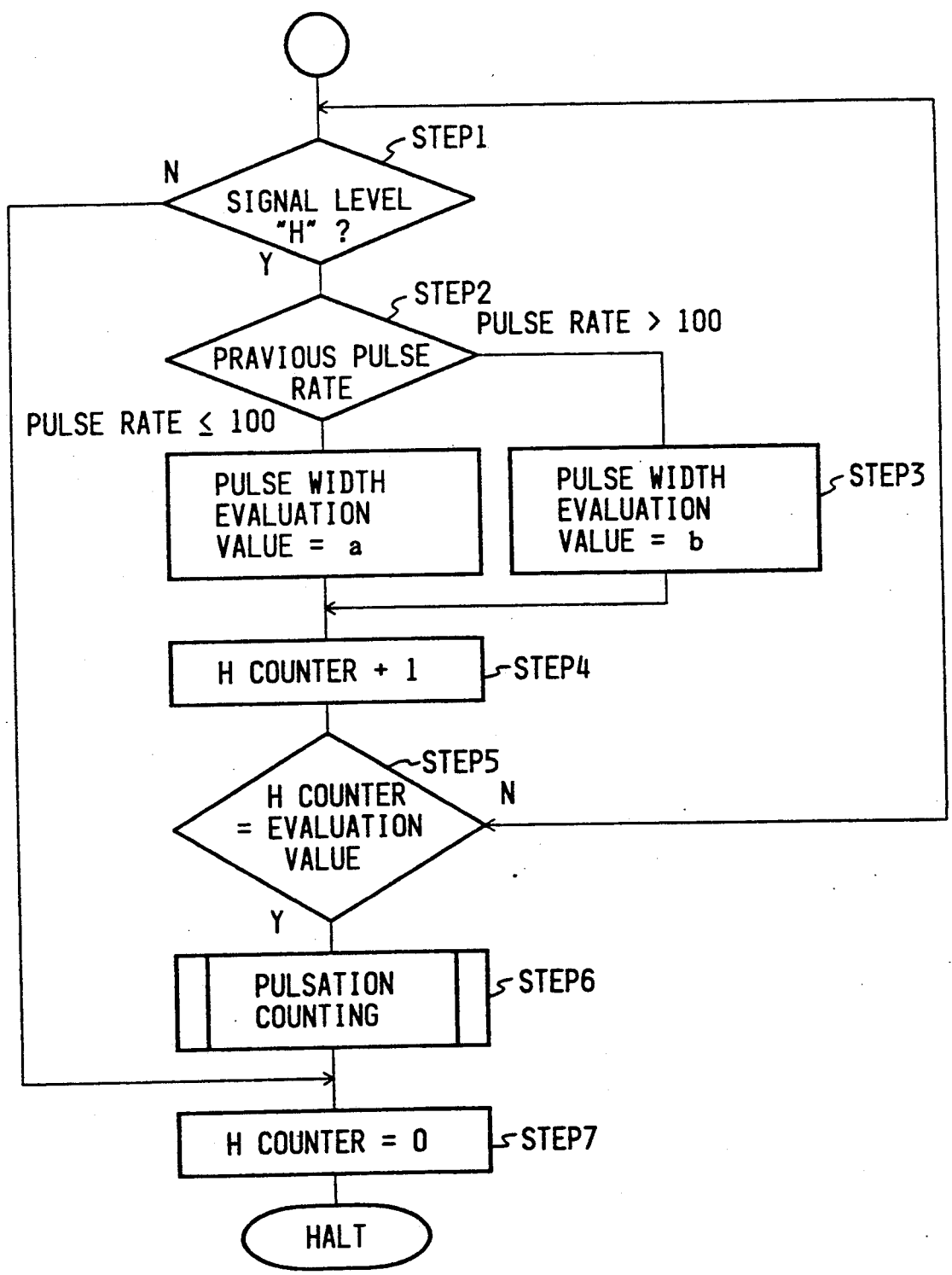
FIG. 7 is a flowchart useful for explaining a second embodiment of the present invention.
Figure 8:
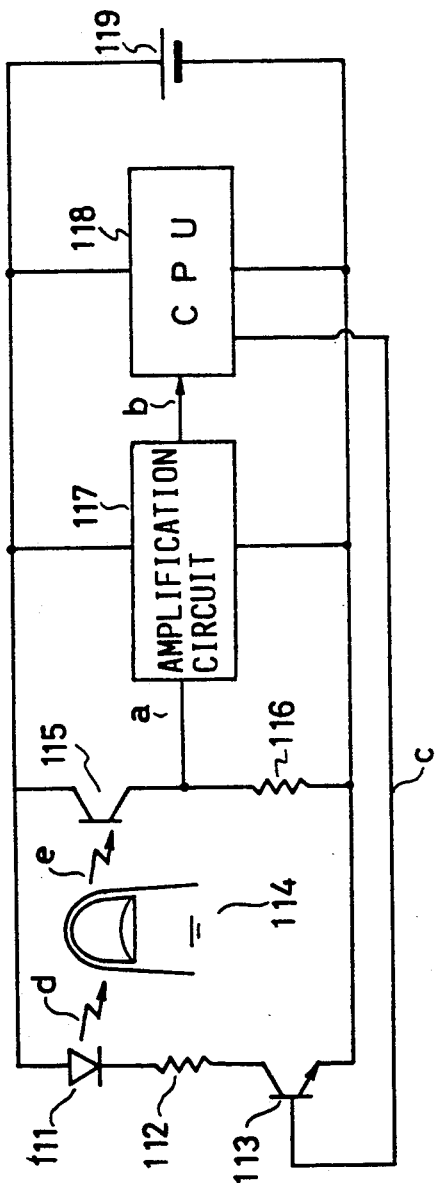
FIG. 8 is a schematic structural view of the photoelectric pulsimeter.
Figure 9:
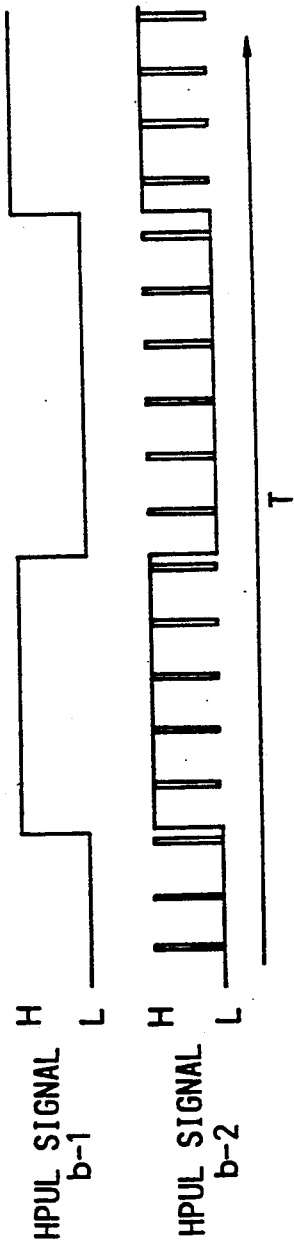
FIG. 9 is a waveform diagram of an HPUL signal.

Next, another embodiment of the present invention will be represented and its operation will be explained. This embodiment represents the case where the pulsation signal pulse width evaluation means and pulsation calculation means described above are accomplished by software processing using, for example, a micro-processor. FIG. 7 shows a flowchart using software to accomplish the functions of the pulsation signal pulse width evaluation means and the pulsation signal calculation means. An interrupt occurs at the beginning of the pulsation signal and the software is started. In the first step STEP 1, the signal level of the pulsation signal is checked and if it is "H", the flow shifts to STEP 2. In this STEP 2, whether or not the previous pulse rate display is above 100 is checked. If it is found to be equal below 100 as the result of check, the pulsation signal pulse width evaluation value is set to a. If it proves above 100, the pulsation signal pulse width evaluation value is set to b. In the next STEP 4, the H counter is incremented by +1. In the next STEP 5, whether or not the the content of the H counter is equal to the predetermined pulsation signal pulse width evaluation value is compared and if it is, the pulsation counting sub-routine is called in the STEP 6 to count the pulse rate. If it is not equal, the flow returns to the STEP 1 and the loop of STEPs 1-5 is repeated until the value of the H counter becomes equal to the pulsation signal pulse width evaluation value. In the mean time, if the pulsation signal pulse falls to "L", the H counter is cleared at the STEP 7 and the flow shifts to HALT. Due to the processing described above, the pulse rate calculation cannot be made unless the pulsation signal has a certain predetermined value. As a result, since the noise having a small pulse width can be neglected, the pulse rate display can be stabilized.

In accordance with the present invention described above, the pulsation signal pulse width evaluation means for evaluating the pulsation signal outputted from the pulsation detection circuit can remove the noise and transmit only the original pulsation signal to the pulsation calculation means. Accordingly, the stability of the pulse rate display can be improved drastically.

Figure 10:
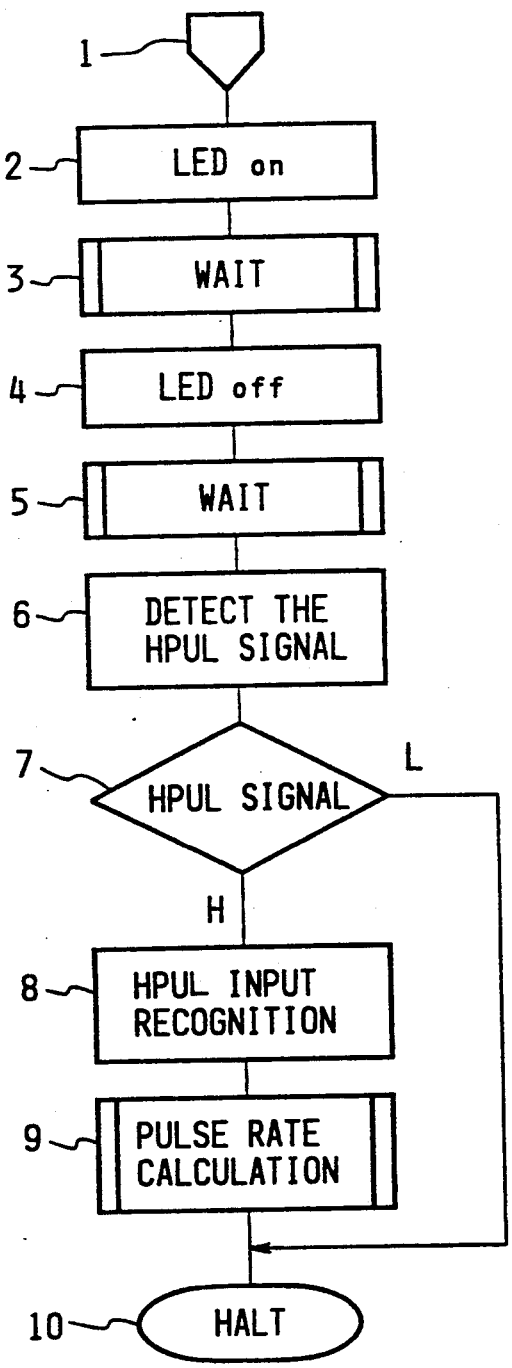
FIG. 10 is a flowchart of detecting the HPUL signal.

FIG. 10 is a flowchart of detecting the HPUL signal when the present invention is practised by programming of a CPU 118.

When a periodical (128 Hz in this embodiment) light emission interrupt is applied in order to let LED 111 cause interrupted light emission, an LED-on command 2 and LED-off command 4 are executed sequentially. An LED-on time is managed as the time where the change of the blood flow rate can be perceived as an electric signal through the light reception device by a WAIT routine 3. There is the possibility that the spike pulse due to the current change remains during this LED-on time. Therefore, level detection of the HPUL signal is not made. Stand-by is then made by the WAIT routine 5 until the power source becomes steady and the spike pulse disappears after LED-off(Step A). Then, the level of the HPUL signal b is detected (step 6). If the HPUL signal b is "L", the pulsation pulse input is not judged as existing and the flow jumps to HALT 10 (step 7). If the HPUL signal b is "H", HPUL input recognition processing, pulse rate calculation processing, etc., for confirming the pulse rate, etc., are executed by assuming that the pulsation pulse is accepted.

In the embodiment described above, level detection of the HPUL signal b is made whenever the LED emits the rays of light but it is also possible to make level detection in a shorter period depending on the accuracy of the pulse rate detection or to detect periods other than the time from LED-on to LED-off and a subsequent specific period.

Next, an embodiment of the hardware of the invention will be explained.

Figure 11:
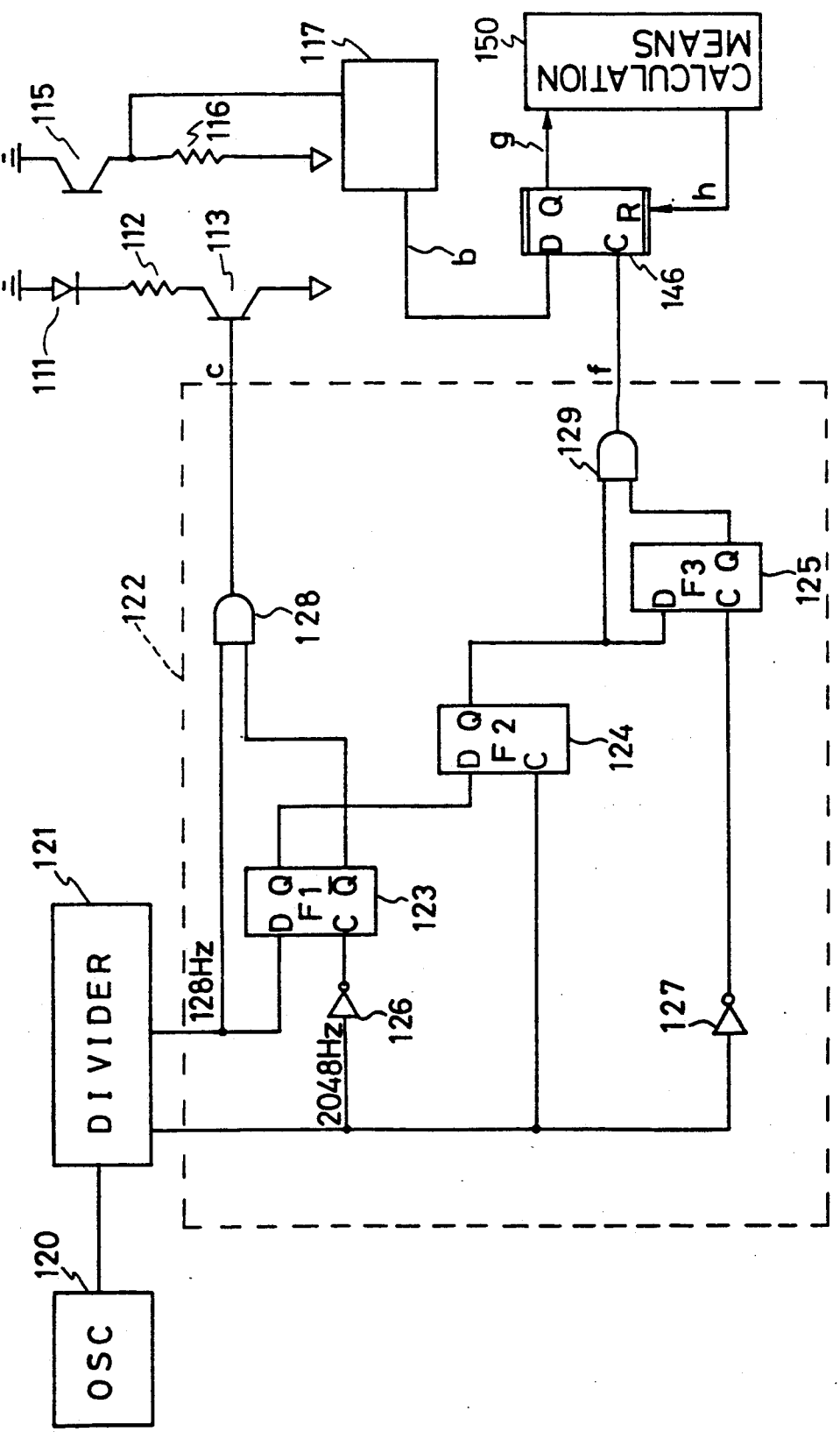
FIG. 11 is a circuit diagram when the present invention is practised hardware-wise.
Figure 12:
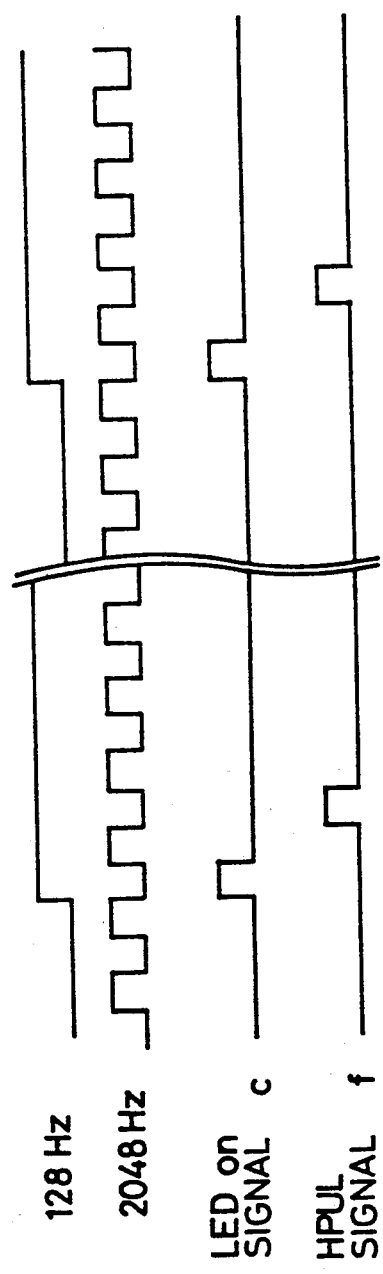
FIG. 12 is a timing chart when the invention is practised hardware-wise.

FIG. 11 is a schematic circuit diagram including pulsation pulse detection means 122. If the LED light emission period is 128 Hz and the LED light emission time is 4096 Hz, for example, the pulsation pulse detection means 122 for inputting 2048 Hz an 128 Hz signals outputted from OSC 120 and a frequency divider 121, respectively, outputs an LED light emission signal c having a pulse width of 4096 Hz in synchronism with the rise of the 128 Hz signal by a NOT circuit 126, a flip-flop circuit 123 and a gate circuit 128. The pulsation pulse detection means 122 also outputs the HPUL detection signal f which is delayed by 4096 Hz from the LED light emission signal c described above by a NOT circuit 127, a flip-flop circuit 124 and 125 a gate circuit 129. FIG. 12 shows the relationship between the LED light emission signal c and the HPUL detection signal f.

The LED light emission signal c described above causes light emission of LED inputted to the switching transistor 113 for LED light emission and the HPUL detection signal f is inputted to the clock of a half latch 126 for generating the HPUL signal with a delay of 4096 Hz. The half latch 126 which uses the HPUL signal b outputted from the amplification circuit 117 as the data, latches the data by the clock signal inputted thereto with the delay of 4096 Hz from the LED light emission period. Therefore, it becomes possible to output only the correct pulsation pulse as the pulsation signal g to the calculation means 127, consisting of a CPU or logic circuit, without using the spike pulse generated during the LED light emission period as the data. After outputting the pulsation signal g, the half latch 146 is reset (h) by the calculation means 127 or the like, and enters the stand-by state to wait for the input of the next HPUL signal.

When the pulsation pulse is detected in the periods other than the LED light emission period by use of the means described above, it becomes possible to prevent erroneous recognition of the spike pulse occurring at the time of the power source voltage as the pulsation pulse. Therefore, the correct pulsation can be detected and displayed stably without being affected by the life of the battery, the ambient temperature, and the like.

What is claimed is:

1. A photoelectric pulsation type pulsimeter comprising:

a pulsation detection circuit for detecting a pulsation pulse of a heartbeat and outputting a pulsation signal to pulse width evaluation means;

pulse width evaluation means for evaluating said pulsation signal and a pulse rate;

pulsation calculation means for calculating said pulse rate;

a reference signal generation circuit for generating a reference signal and outputting said reference signal to said pulsation calculation means and said pulse width evaluation means; and display means for displaying said pulse rate calculated by said pulsation calculation means.

2. A photoelectric pulsation type pulsimeter according to claim 1; wherein said pulse with evaluation means includes means for evaluating plural evaluation reference values.

3. A photoelectric pulsation type pulsimeter according to claim 2; wherein said plural evaluation reference values change with respect to said pulse rate calculated by said pulsation calculation means.

4. A photoelectric pulsation type pulsimeter according to claim 1; wherein said pulse width evaluation means includes storing means for storing a minimum evaluation reference value and selecting means for selecting an evaluation reference value from stored data of said storing means.

5. A photoelectric pulsation type pulsimeter according to claim 1; wherein said pulsation detection circuit includes a light emission device.

6. A photoelectric pulsation type pulsimeter according to claim 5; wherein said pulsation detection circuit includes pulsation pulse detection means for detecting said pulsation pulses in a period other than the turn-on period of said light emission device.

7. A pulsimeter, comprising: detecting means including a pulsation detection circuit for detecting a pulse and generating a pulsation signal in response thereto; pulse width evaluation means for evaluating the pulsation signal with an evaluation reference value and generating a recognized pulsation signal in response thereto; pulsation calculation means for calculating a pulse rate dependent on the recognized pulsation signal; and display means for displaying the pulse rate.

8. A pulsimeter according to claim 7; further comprising reference signal generating means for generating a reference signal; and wherein the pulse width evaluation means includes means for determining the evaluation reference value dependent on the pulse rate and the reference signal.

9. A pulsimeter according to claim 7; wherein the pulse width evaluation means includes means for evaluating plural evaluation reference values dependent on the pulse rate.

10. A pulsimeter according to claim 7; wherein the pulse width evaluation means includes storing means for storing a minimum evaluation reference value and selecting means for selecting an evaluation reference value from data stored in the storing means.

11. A pulsimeter according to claim 7; wherein the detecting means includes a light emission device.

12. A pulsimeter according to claim 11; wherein the pulsation detection circuit includes pulsation pulse detecting means for detecting the pulse in a period other than a turn-on period of the light emission device.

* * * * *